US006197522B1

(12) United States Patent
Keller et al.

(10) Patent No.: US 6,197,522 B1
(45) Date of Patent: Mar. 6, 2001

(54) METHOD FOR IDENTIFYING AND QUANTIFYING POLYMERS UTILIZING IMMUNOASSAY TECHNIQUES

(75) Inventors: Lorraine Holowach Keller, Lansdale; Barry Weinstein, Dresher, both of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 08/783,727

(22) Filed: Jan. 16, 1997

Related U.S. Application Data
(60) Provisional application No. 60/010,184, filed on Jan. 18, 1996.

(51) Int. Cl.[7] .................. G01N 33/53; G01N 33/532; G01N 33/531
(52) U.S. Cl. .................. 435/7.1; 435/7.9; 435/7.92; 436/544; 436/547; 436/543
(58) Field of Search .................. 436/531, 547, 436/548, 544, 543, 518, 815; 435/7.9, 7.1, 7.92, 975, 7.93, 7.94; 530/388.9, 389.1, 389.8, 387.1, 388.1, 388.85

(56) References Cited

U.S. PATENT DOCUMENTS

| | | | |
|---|---|---|---|
| 4,046,707 | * 9/1977 | Smith et al. | 252/180 |
| 4,636,478 | 1/1987 | Siebert et al. | |
| 5,153,312 | * 10/1992 | Porro | 530/405 |
| 5,171,450 | * 12/1992 | Hoots | 210/701 |
| 5,294,371 | 3/1994 | Clubley et al. | |
| 5,298,585 | 3/1994 | McCallum, III et al. | |
| 5,376,731 | 12/1994 | Kerr et al. | |
| 5,386,038 | * 1/1995 | Davis et al. | 549/262 |
| 5,412,051 | * 5/1995 | McCallum et al. | 526/317.1 |
| 5,429,952 | 7/1995 | Garner et al. | |
| 5,576,002 | * 11/1996 | Jennings et al. | 424/197.11 |
| 5,593,850 | * 1/1997 | Wetegrove et al. | 435/7.92 |
| 5,763,249 | * 6/1998 | Schultz et al. | 435/188.5 |
| 5,866,664 | * 2/1999 | McCallum, III et al. | 526/233 |
| 5,925,716 | * 7/1999 | Fu et al. | 55/329.7 |

FOREIGN PATENT DOCUMENTS

| | | |
|---|---|---|
| 2004420 | 12/1989 | (CA). |
| 0 327 163 A2 | 9/1989 | (EP). |
| 0 475 602 | * 3/1992 | (EP). |
| 0 535 347 | * 4/1993 | (EP). |
| 0 540 314 A1 | 5/1993 | (EP). |
| 0 535 347 A2 | 7/1993 | (EP). |
| 0 559 249 A1 | 8/1993 | (EP). |
| WO 95/06249 | 3/1995 | (WO). |

OTHER PUBLICATIONS

Jennings et al. J. Immunol. 127: 1011–1018, 1981.*
Devi et al. FEMS Immunol. Med. Microbiol. 14: 211–20, 1996.*
Ashton et al. Microb. Pathogen. 6: 455–458, 1989.*
Sudi et al. Kieler Milchietschafliche Forschugsberichie 40: 179–03, 1988.*
Seki et al. Cancer Res. 46: 907–916, abstract, 1986.*
Tramontano et al. PNAS 83: 6736–6740, abstract, 1986.*
Kimura et al. Japanese J. Allergology 39 (7): 587–594 (abstract), 1990.*
Larkin et al. In: Field screening methods for hazardous wastes and toxic chemicals. VIP–47, vol. 2, p. 1031, 701 p (abstract), 1995.*
Matsuhita Electrical Industrial Co. Ltd., Comline Biotechnology and Medical, Jan. 23, 1989, p. 1, (abstract).*
Abuharfeil et al. Electrophoresis 12 (9): 683–684 (abstract), 1991.*
Bartoloni et al. Vaccine 13 (5): 463–470, 1995.*
De Boos. Polymer 14: 587–588, 1973.*
"Doing immunoassays in the field", Stephen B. Friedman, *Chemtech* Dec. 1992.
"You're Polluted. You're Not.", Patrice Courtney, *Resources* Jun. 1994.
"Monoclonal Antibodies: A Manual of Techniques", Hedda Zola.
"Environmental monitoring by immunoassay", Martin Vanderlann, et al., *Environmental Science & Technology*, vol. 22, No. 3, 1988, 247–254.

* cited by examiner

*Primary Examiner*—James Housel
*Assistant Examiner*—S. Devi
(74) *Attorney, Agent, or Firm*—Thomas J. Howell

(57) ABSTRACT

Disclosed is a method for quantitatively identifying polymers in an aqueous system using immunoassay techniques, wherein at least a portion of the polymers contain a detectable terminus. This is particularly useful in water treatment systems. Also disclosed are new hybridoma cell lines which express MAbs which specifically recognize such a detectable terminus.

11 Claims, 1 Drawing Sheet

METHOD FOR IDENTIFYING AND QUANTIFYING POLYMERS UTILIZING IMMUNOASSAY TECHNIQUES

This application claims the benefit of provisional application Ser. No. 60/010,184, filed Jan. 18, 1996.

BACKGROUND OF THE INVENTION

The present invention relates to a method for identifying and quantifying polymers in aqueous systems by utilizing immunoassay techniques. In particular, monoclonal antibodies ("MAbs") are created against: an initiator (or fragment thereof) used to start the polymer process; a chain transfer agent used in the polymerization process to prepare the polymer being detected; or a functional group which can be subsequently attached to a chain transfer agent. The present invention also relates to new hybridomas (immortalized cell lines) which express these MAbs. The present invention is particularly useful for determining the concentration of polymers used in water treatment applications.

Water-soluble polymers are used in many aqueous systems, for example: as mineral dispersants; as water-treatment additives for boiler waters, cooling towers, reverse osmosis applications, sugar refining, paper production, geothermal processes, and oil wells; and as detergent additives acting as builders, anti-filming agents, dispersants, sequestering agents, and encrustation inhibitors. In these types of applications, the polymers complex with minerals or other substances to remove them from the water, for example, to prevent corrosion and mineral deposits (scale) in water-treatment applications. Over time, as the complexation sites on the polymer become saturated, the polymer becomes inactivated or decomposes, and more active polymer must be added. This is particularly important in water-treatment applications, where insufficient active polymer can result in the water treatment being overwhelmed by dissolved minerals, causing severe corrosion or scale deposits, and where maintenance of a higher than necessary active polymer concentration is costly and inefficient. It is therefore desirable to be able to detect readily the polymer concentration within a system at various times, in order to determine whether or not additional polymer should be added.

One of the problems associated with detecting polymers in aqueous systems is the lack of sensitivity in traditional detection methods such as calorimetric or fluorimetric assays, since the polymers are generally present at very low levels, from 500 down to less than 5 parts per million ("ppm"). Another problem associated with detecting polymers in aqueous solutions is that the detection methods frequently lack selectivity and may give false results for components of the aqueous system other than polymers.

Attempts to overcome these problems have included methods for manufacturing MAbs against portions of the product polymers, then using these MAbs to detect the presence or concentration of product polymer using immunoassay techniques. Such methods are disclosed and discussed in, for example, EP 540 314 A1 (Wetegrove, et al.), EP 535 347 A2 (Wetegrove, et al.), and EP 559 249 A1 (Weatherby, et al.). In all of these methods, the MAbs bind to selected sites on the polymer, but one-to-one correspondence between the MAb and a particular polymer strand is unlikely due to the great number of repeating units within a polymer chain; moreover, since the polymers are of varying chain lengths, there will be a variation in the number of MAbs binding to each polymer. Thus, determination of MAb to polymer concentration ratio will be batch dependent (i.e., the ratio will vary depending on the particular batch of polymer prepared), and accuracy of such measurements may vary relatively widely.

PCT US94/09264 (Garner, et al.) discloses a method for marking products for later identification. This method involves creating a low molecular weight hapten, covalently bonding such hapten to a carrier compound, and associating such hapten-labeled compound with the product, such that the hapten serves as a marker which can later be detected using immunoassay techniques. The carrier compound can be a polymer, such that the hapten is either attached to the already formed polymer, or the hapten can be attached to the monomer prior to polymerization. To be useful in this method, a hapten-labeled compound (the "marker compound") is non-deleterious to the product, is inert with respect to the product, and is not already be associated with the product. The marker compound is generally associated with the product by mixing the marker compound with product, but it can be present in the product packaging or labeling.

Although Garner, et al. disclose that the "use of this tagged compound in a fixed ratio to untagged compound allows for tracing of the tagged compound," the nature of their method precludes quick and convenient determination of product concentration where the product is a polymer. Garner, et al. teach that the hapten can be attached to the already formed polymer, or to the monomer prior to polymerization; however, in either case, it will not be possible to determine absolutely the hapten:polymer ratio, since the length of each polymer chain is not constant, and the number of haptens attached to each particular polymer chain will vary. Thus, the hapten:polymer ratio will be batch-dependent, making detection of polymer concentration difficult: standard concentration curves will have to be run for each batch of tagged polymer; the polymer added to the system is unlikely to be from the same batch as the previously added polymer, possibly affecting the calibration and accuracy of the assay; and the total polymer concentration in a system will likely be composed of polymers from various batches rather than only one batch, also possibly affecting the calibration and accuracy of the assay.

STATEMENT OF THE INVENTION

A method for identifying and quantifying polymers in an aqueous system wherein at least a portion of the polymers contain a detectable terminus selected from a chain transfer agent, an initiator or initiator fragment, or a group attached to the chain transfer agent, such method comprising the steps of: a) producing a monoclonal or polyclonal antibody to the detectable terminus; b) obtaining a sample of the aqueous system to be tested, and incubating the sample with the monoclonal or polyclonal antibody; and c) detecting and measuring the degree of binding of the monoclonal or polyclonal antibody to identify the polymers and to determine the polymeric concentration in the aqueous system.

DETAILED DESCRIPTION OF THE INVENTION

Figure 1:
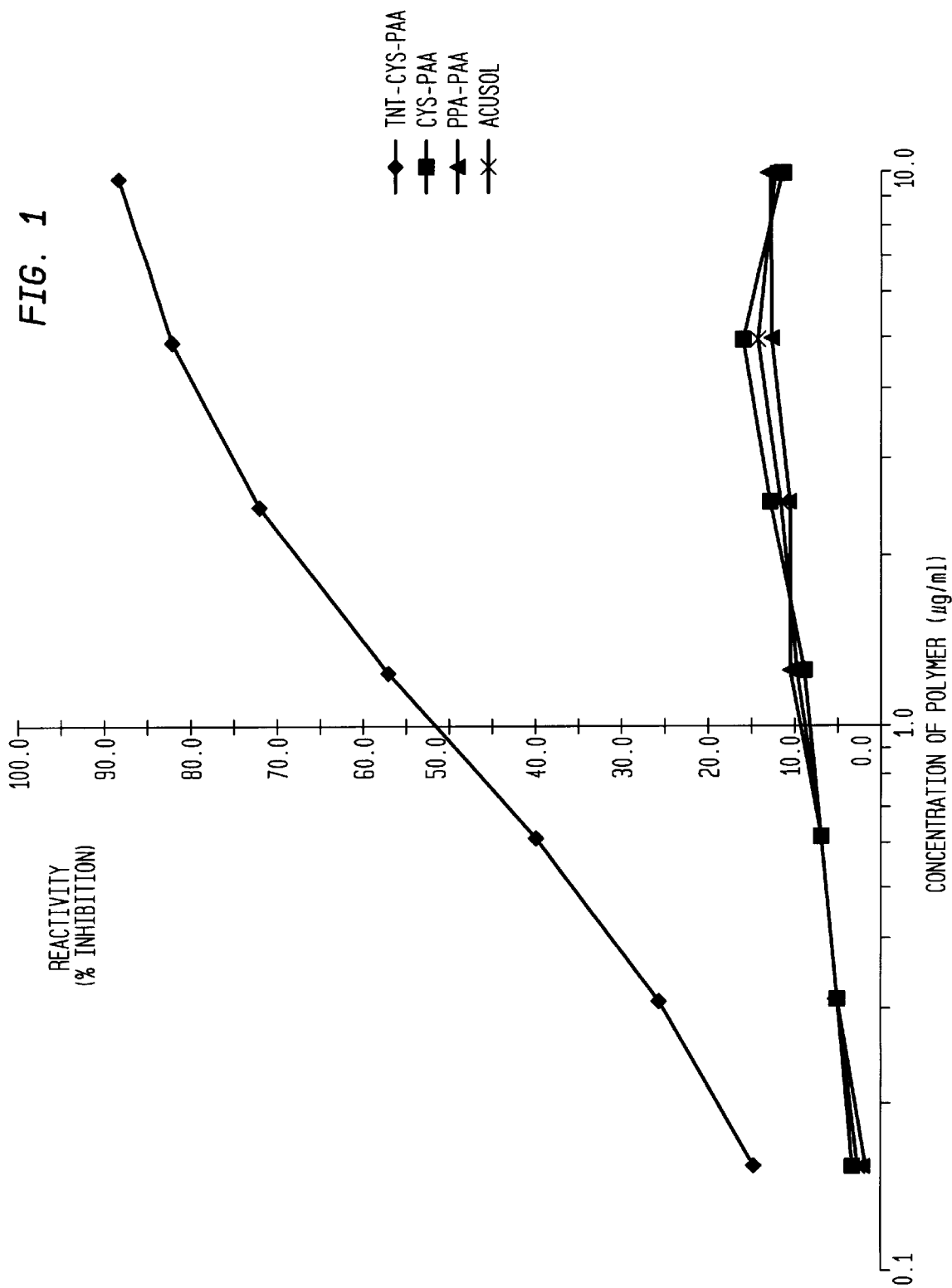
FIG. 1 is a graph plotting concentration of polymer ($\mu$g/mL) versus reactivity (% inhibition), and illustrates the reactivity of various polymers in a TNT-Tag immunoassay. The legend for the graph is as follows: —♦—=TNT-CYS-PAA; —■—=CYS-PAA; —▲—=PPA-PAA; and —×—= Acusol® 445N. (PAA)

As used in this specification, the following terms have the following definitions, unless the context clearly indicates otherwise. "Immunogenic antigen" or "immunogenic molecule" refers to a substance which, when introduced into an animal with a functioning immune system, elicits an immune response leading to a state of immunity. "Antigenic determinant" or "epitope" refers to a portion of an immunogenic molecule which specific antibodies recognize. "Hapten" is a low molecular weight molecule that is not intrinsically immunogenic, but can serve as part of an antigenic determinant on an immunogenic molecule; that is, if these haptens are first coupled with an immunogenic antigen, antibodies can be formed against various portions of the complex, including some which will specifically bind to the haptens. "Tag" refers to a detectable terminus on the polymer chain to which monoclonal or polyclonal antibodies have been developed, wherein the detectable terminus is selected from a chain transfer agent, an initiator (or fragment thereof), or a group attached to the chain transfer agent; and "Tagged" used in reference to a polymer means that the referenced polymer contains a Tag. Ranges specified are to be read as inclusive, unless specifically identified otherwise.

In a free-radical polymerization process where a chain transfer agent is employed, the polymerization reaction is terminated by the chain transfer agent. The radical thus produced becomes the beginning of a new polymer chain. Where there is only a limited amount of polymeric branching (as is usually the case with low molecular weight (less than 50,000) polymers—typical for anti-scalants), the ratio of chain transfer agent to polymer chain is about 1 to 1; thus, a method of detecting the concentration of Tagged polymer will result in a direct determination of the total concentration of polymer in the system. The method of the present invention provides such an easy, efficient way to detect polymer concentration by detection of the Tag, using sensitive and selective immunoassay techniques.

All of the polymers used in an aqueous system can be Tagged, or a specified portion of the polymers can be Tagged. It is preferred to Tag only a small percentage of the polymers in a system. Where only a portion of the polymer is Tagged, the unTagged polymer is not required to be the same as the Tagged polymer, but it is preferred that the unTagged and the Tagged polymers perform similarly in the system, such that the rate of depletion of the Tagged polymer accurately reflects the rate of depletion of the entire system.

The Tagged polymers of the present invention can be any type polymerizable with a chain transfer agent, typically vinyl polymerization. In one embodiment of the present application where the Tagged polymers of the present invention are used for detecting water treatment polymers, it is preferred to use polymers or copolymers of polycarboxylic acids, especially acrylate polymers and derivatives thereof. Particularly useful acrylate polymers include polymers and copolymers made from monomers of ethylenically unsaturated monocarboxylic acids containing 3–5 carbon atoms per molecule, and ethylenically unsaturated dicarboxylic acids containing 4–8 carbon atoms per molecule, as well as their alkali metal and ammonium salts, and the anhydrides of the cis dicarboxylic acids. Examples of monocarboxylic acids include, but are not limited to: acrylic acid, methacrylic acid ("AA"), vinylacetic acid, crotonic acid, and acryloxypropionic acid Of these, acrylic acid ("AA") and methacrylic acid are preferred. Examples of suitable dicarboxylic monomers include, but are not limited to: maleic acid, itaconic acid, mesaconic acid, fumaric acid, citraconic acid, tetrahydrophthalic acid, tetrahydrophthalic anhydride, and maleic anhydride. Among the dicarboxylic monomers, maleic anhydride is preferred.

The starting polymer may additionally be composed of up to 70 percent by weight ("wt %") of acid-free monoethylenically unsaturated monomers, so long as the polymer remains water-soluble. Such other monomers include, but are not limited to: alkyl esters of acrylic or methacrylic acid, such as methyl acrylate, ethyl acrylate, butyl acrylate, methyl methacrylate, ethyl methacrylate, butyl methacrylate, and isobutyl methacrylate; hydroxyalkyl esters of acrylic or methacrylic acid, such as hydroxyethyl acrylate, hydroxypropyl acrylate, hydroxyethyl methacrylate, and hydroxypropyl methacrylate; other types of acrylates or methacrylates, such as 2-sulfoethyl(meth)acrylate, 3-sulfopropyl(meth)acrylate, 2-sulfatoethyl(meth)acrylate, dimethylaminoethyl acrylate and phosphoethyl menthacrylate; acrylamides and alkyl-substituted acrylamides such as methacrylamide, t-butylacrylamide, N-t-butyl-acrylamide, N-methyl acrylamide, N,N-dimethylacrylamide, and 3-N,N-dimethylaminopropylacrylamide; acrylonitriles such as methacrylonitrile; allyl alcohol; allyl sulfonic acid; allyl phosphonic acid; vinylphosphonic acid; 2-vinylpyridene; 4-vinylpyridene; N-vinyl pyrrolidone; N-vinylformamide; N-vinylimidazole; N-acrylomorpholine; acrolein; ethylene glycol diacrylate; trimethylolpropane triacrylate; diallyl phthalate; vinyl acetate; styrene; vinylsulfonic acid, p-styrenesulfonic acid, and 2-acrylamido-2-methylpropanesulfonic acid; methallyl sulfonate and 1-allyloxy-2-hydroxypropyl sulfonate (COPS®); acrylamidoglycolic acid; and salts of the above, as appropriate.

The starting polymer is most preferably polyacrylic acid ("PAA"), or a copolymer of acrylic acid and maleic acid or maleic anhydride. In addition, it is preferred that the number average molecular weight ("Mn") of the starting polymer or copolymer be in the range of 500–100,000, more preferably 1000–50,000, and most preferably 2000–25,000.

Any chain transfer agent useful in controlling the molecular weight of polymer compositions can be used as a Tag in the present invention. Such chain transfer agents include, but are not limited to: mercaptans, phosphinates, phosphonates, sulfinic acids (such as phenylsulfinic acid and p-toluenesulfinic acid), and amine-thiols. Suitable phosphinates include those disclosed as compounds of formula I (col. 1) in U.S. Pat. No. 5,294,371 (Clubley, et al.) and those disclosed as compounds of formula III (col. 4) in U.S. Pat. No. 5,376,731 (Kerr, et al.), and suitable amine-thiols include the type disclosed in U.S. Pat. No. 5,298,585 (McCallum, et al.). These three patents are incorporated by reference herein to the extent they describe these types of chain transfer agents and processes for preparing them. It is preferred to use cysteine ("CYS"), aminoethane thiol ("AET"), or phenylphosphinic acid ("PPA") as the chain transfer agent.

Any initiator or initiator fragment useful in initiating free radical addition polymerization can be used as a Tag in the present invention. Such initiator or initiator fragments include, but are not limited to: peroxyesters, such as t-butylperbenzoate and t-amylperoxybenzoate; dialkylperoxides, such as dicumylperoxide; diacylperoxides, such as benzoyl peroxide; hydroperoxides, such as cumene hydroperoxide; azo compounds, such as 2-phenylazo-4-methoxy-2,4-dimethyl-valeronitrile, 2,2'-azobis-2-methyl-N-phenylpropionamidine dihydrochloride, 2,2'-azobis-2(N-(4-chlorophenyl)-2-methylpropionamidine) dihydrochlioride, 2,2'-azobis(2-(5-methyl-2-imidazoline-2-yl)propane) dihydrochloride, and 2,2'-azobis(2-(2-imidazolin-2-yl) propane) dihydrochloride.

Where the Tag is a group attached to the chain transfer agent, the chain transfer agent of choice is an amine-thiol, especially CYS or AET. Groups which can be attached to such chain transfer agents are those which will react specifically with the desired group, but not with other portions of the polymer. When the chain transfer agent contains a pendant amine, it is preferred to attach amine-reactive groups to them as Tags. Preferred amine-reactive groups include but are not limited to: 1-(dimethylamino)-5-naphthalenesulfonic acid and its halides ("dansyl"); 4-dimethylaminoazobenzene-4-sulfonic acid and its halides ("dabsyl"); 2,4,6-trinitro-benzenesulfonic acid and its salts ("TNT"); 3-benzoylquinoline-2-carboxaldehyde; 3-(2-furfoyl)quinoline-2-carboxaldehyde; 2,4-dinitrofluorobenzene (Sanger's reagent); and ninhydrin. Particularly preferred groups include: daisyl, dabsyl, and TNT.

The monoclonal and polyclonal antibodies of the present invention may be produced by techniques known to those skilled in the art. There are many techniques for producing polyclonal antibodies, including those techniques described by B. A. L. Hurn and S. M. Chantler, "Production of Reagent Antibodies," *Methods of Enzymology*, 70:104–142 (1980). The technique for producing MAbs was first described by G. Kohler and C. Milstein in *Nature*, 265: 495 (1975). it is preferred to use MAbs in the immunoassay techniques of the present invention.

For production of MAbs specific against particular Tags, antibodies are first produced in a mouse by inoculating it with an immunogenic conjugate of the Tag (typically, the immunogenic conjugate is the Tag attached to an immunogenic molecule). Multiple inoculations are made over a period of 1 to 300 days or more. Inoculations can be made using any of a number of routes, including intraperitoneal, intravenous, or subcutaneous injections, with doses of 5–50 micrograms ("$\mu$g") of conjugate per injection. The conjugate may be injected alone, or combined with other substances to increase the immunogenicity of the conjugate. At the end of the immunization period, lymphocytes from the spleen are collected, and fused with myeloma tumor cells to form hybridomas. These hybridomas are then separated, cultured, and tested, to determine which hybridomas have the required specificity and affinity for the Tag. MAbs from these selected hybridomas are then grown in vitro or in vivo according to techniques known to those skilled in the art.

The hybridomas of the present invention include those designated Hybrid1, Hybrid2, and Hybrid3, obtained by immunization of Swiss or Balb/c mice. The MAbs elaborated by these hybridomas react with the PPA alone, 2-carboxypropyl-(phenyl)phosphinic acid (essentially, PPA plus one unit of AA), or Tagged polymer (PPA-PAA) at concentrations as low as 1 ppm, but have little or no affinity to the unTagged polymers (PAA). These MAbs are suitable for use in the immunoassay detection methods of the present invention, including direct sandwich, indirect sandwich, and competitive ELISA assays. It is preferred to use the direct sandwich ELISA.

In the competitive assay, first the antigen is adsorbed onto the plastic support, then free (unbound) antigen is added (usually from a standard solution), followed by addition of the antibody, then the solution is incubated. When the solution is washed away at the end of the incubation period, only the antibodies attached to the bound antigen remain and are detected. The concentration of antibody remaining is inversely proportional to the concentration of the hapten in the sample.

For the non-competitive assays, two different antibodies, each directed to a different epitope on the antigen, are used—one antibody binds the antigen to the solid matrix, and the second is used to detect the antigen and measure its concentration. In the direct sandwich, a detectable label is directly attached to the second antibody; whereas in the indirect sandwich, the second antibody is itself measured using a labeled anti-immunoglobulin.

The MAbs expressed by the hybridoma cells having required specificity and selectivity for the Tags ("anti-Tag MAbs") are useful in the immunoassay detection methods of the present invention. Typically, the appropriate hybridoma line(s) are selected, and the MAbs expressed by these lines are used as reagents and optimized for the particular immunoassay, according to techniques known to those skilled in the art.

The following abbreviations are used in the examples below. L=liter; mL=milliliter; $\mu$L=microliter; g=gram; $\mu$g=microgram; M=molar; mM=millimolar; rpm=revolutions per minute, and nm=nanometer. KLH=keyhole limpet hemocyanin; BSA=bovine serum albumin; OVA=ovalbumin; and AP=alkaline phosphatase. CFA=Complete Freund's Adjuvant; and IFA="Incomplete" Freund's Adjuvant. In addition, the following reagents are used in the examples below. PBS: 13.8 mM NaCl+2.7 mM KCl, pH 7.4. 10× PBS (10 L): 138 mM NaCl (800 g)+2.7 mM KCl (20 g)+4.28 mM NaPO$_4$, dibasic 7 H$_2$O (115 g)+1.46 mM KPO$_4$ (20 g), pH 7.2. PT (20 L): 10× PBS (2 L)+5% Tween® 20 (200 mL)+Water (q.s.). PCT (1 L): PBS (990 mL)+casein (10 g)+5% Tween® 20 (10 mL), pH 7.2. tissue culture medium (1 L): fetal bovine serum (10%) +L-glutamine (1%)+2-mercapthanol (6%)+Iscove's modified Dulbecco's medium (q.s.). TMB: 3,3',5,5'-tetramethylbenzidine (0.4 g/L) in an acidic buffer. All % in this paragraph are by volume.

EXAMPLE 1
Preparation of Immunoconjugates

A. Preparation of TNT-enzyme conjugates (DNP-AP)

TNT-enzyme conjugates were prepared by adding a derivative of TNT (dinitrobenzenesulfonic acid) at various (w/w) ratios, to alkaline phosphatase (AP). The unreacted haptens were removed by extensive dialysis against buffer.

B. Preparation of PPA-PAA-protein conjugates

Acrylic acid moieties of plenylphosphinic acid (PPA) modified polymers (wherein PPA is used as the chain transfer agent) were activated with various molar ratios of carbodiimide, then these activated polymers were added to a carrier protein (chosen from: KLH, BSA, OVA or AP), at various (w/w) ratios, to yield the appropriate PPA-PAA-protein conjugates. The unreacted haptens were removed by extensive dialysis against PBS. For comparison purposes, PPA-protein conjugates were also prepared in a similar manner.

EXAMPLE 2
Preparation of MAbs

For each group of five mice, one of the immunoconjugates of Example 1B was injected over a three month period, in accordance with the following immunization protocol.

At approximately two months after birth, five Swiss mice were bled (tail vein bleeding), the blood pooled, and serum assayed. About two weeks later, a mixture of 0.1 mL of antigen (immunoconjugate) emulsified in 0.1 mL of CFA in saline was injected into the peritoneal cavity of each mouse. At subsequent two week intervals, for about three months, mixtures of 0.1 mL of antigen in saline were emulsified in 0.1 mL of IFA, and injected intraperitoneally into the mice. Blood samples were taken at one-month intervals, and at the conclusion of the immunization period, in order to monitor antibody levels.

Upon conclusion of the immunization period, the sensitized lymphocytes were harvested from the spleen and fused with myeloma cells to form the hybridoma cells. Any of a large number of myeloma cell lines are useful, but a preferred cell line is P3×63Ag8.653. Such fusion protocols are known to those skilled in the art; for example, as described by Kearney, et al., *J. Immunol.*, 123:1548 (1979). Briefly, the lymphocytes and the myeloma cells are combined in the presence of polyethylene glycol for a period of time, cultured, and tested for specificity to various portions of the antigen.

EXAMPLE 3

Testing MAb Specificity

A competition assay was performed using polymers tagged with various endgroups.

TNT-CYS-polymer (the Tagged polymer) was prepared by reacting the amino terminus of a cysteine-modified polymer with 2,4,6-trinitrobenzenesulfonic acid. Unreacted 2,4,6-trinitrobenzenesulfonic acid was removed by diafiltration using an Amicron® microconcentrator. Such cysteine-modified polymers (wherein cysteine is used as the chain transfer agent) are described in McCallum, et al., referenced earlier.

Immulolon-2 plates were coated with 100 μL/well of purified anti-TNT MAb at 5 μg/mL in 0.1M carbonate buffer (pH 9.6), and the plates incubated overnight at 4° C., or for 1 hour at 37° C. After incubation, the plates were washed three times with PT, rotated 180°, and washed another three times with PT. At this point, 125 μL/well of PCT was added, and the plates incubated for 1 hour at room temperature on a plate shaker set at 120 rpm. After incubation, the plates were washed three times with PT, rotated 180°, and washed another three times with PT. Inhibition solutions of TNT-CYS-polymer, CYS-PAA, PPA-PAA, and Acusol® at various concentrations were prepared, and each of these inhibition solutions were added to a well simultaneously with a 1:75 dilution of DNP-AP. The plates were then incubated for 1 hour at room temperature on a plate shaker set at 120 rpm. After incubation, the plates were washed three times with PT, rotated 180°, and washed another three times with PT. To each well was then added 100 pL of p-nitrophenyl phosphate (PNPP) diluted in diethanolamine substrate buffer. Then the plates were incubated for an additional 15 minutes at room temperature on a plate shaker set at 120 rpm. Last, the plates are read using a fluoronmeter set at 405 nm.

FIG. 1 shows the results of this experiment. The data plotted clearly demonstrate that TNT-CYS-PAA was readily detectable at concentrations ranging from 0.1 to 10 μg/mL, while similar concentrations of CYS-PAA, PPA-PAA, and Acusol® 445N gave minimal responses. Moreover, the data of FIG. 1 show that, at least within the tested concentration range, there is a linear relationship between reactivity and polymer concentration.

What is claimed is:

1. A method for identifying and quantifying polymers in an aqueous solution, wherein said polymers are produced by chain polymerization, and wherein said method comprises the steps of:

a. obtaining a sample of said aqueous solution, wherein at least a percentage of the total said polymers in said solution are detectable polymers, each said detectable polymer having a single detectable terminus, which terminus is selected from the group consisting of a chain transfer agent, a chain initiator, a chain initiator fragment, and a group attached to said chain transfer agent;

b. incubating said solution with an antibody which specifically binds to said detectable terminus; and c. detecting and measuring the degree of binding of said antibody to the detectable termini in said solution, wherein said binding indicates the concentration of said detectable polymers and permits the measurement of the concentration of polymers in said solution.

2. The method according to claim 1, wherein said chain transfer agent is selected from the group consisting of a mercaptan, a phosphinic acid, a phosphonic acid, a sulfinic acid, an amine-thiol, and a salt thereof.

3. The method according to claim 1, wherein said chain transfer agent comprises an amine-thiol.

4. The method according to claim 1, wherein said initiator or initiator fragment is selected from the group consisting of a peroxyester, a dialkylperoxide, a diacylperoxide, a hydroperoxide and an azo compound.

5. The method according to claim 1, wherein said detectable terminus comprises an amine-reactive group attached to a chain transfer agent.

6. The method according to claim 5, wherein said chain transfer agent comprises an amino-thiol.

7. The method according to claim 5, wherein said amine-reactive group is selected from the group consisting of 1-(dimethylamino)-5-naphthalenesulfonic acid, a halide thereof, 4-dimethylaminoazobenzene-4-sulfonic acid, a halide thereof; 2,4,6-trinitrobenzenesulfonic acid, a salt thereof; 3-benzoylquinoline-2-carboxaldehyde; 3-(2-furfoyl) quinoline-2-carboxaldehyde; 2,4-difluoronitrobenzene; and ninhydrin.

8. The method according to claim 1, wherein said antibody is a polyclonal antibody.

9. The method according to claim 1, wherein said antibody is a monoclonal antibody.

10. The method according to claim 1, further comprising the step of producing said antibody to said detectable terminus, said further step being performed no later than said incubating step of claim 1.

11. The method according to claim 1, wherein said detecting and measuring step comprises performing an enzyme-linked immunosorbent assay to detect and measure the degree of binding of said antibody to said detectable termini in said solution.

* * * * *